(12) United States Patent
Ueda et al.

(10) Patent No.: US 6,427,519 B2
(45) Date of Patent: Aug. 6, 2002

(54) ROAD SURFACE FRICTION MEASURING METHOD AND DEVICE THEREFOR

(75) Inventors: Tetsuhiko Ueda, Tokyo; Tokuo Sotozaki, Higashikurume; Takashi Kai, Tokyo, all of (JP)

(73) Assignee: National Aerospace Laboratory of Science & Technology Agency, Chofu (JP)

( * ) Notice: Subject to any disclaimer, the term of this patent is extended or adjusted under 35 U.S.C. 154(b) by 0 days.

(21) Appl. No.: 09/739,908

(22) Filed: Dec. 20, 2000

(30) Foreign Application Priority Data

Dec. 24, 1999 (JP) .......................................... 11-366897

(51) Int. Cl.⁷ .............................................. G01N 19/02
(52) U.S. Cl. ................................................ 73/9; 73/8
(58) Field of Search ................... 73/9, 862.03, 862.322, 73/146, 128, 129

(56) References Cited

U.S. PATENT DOCUMENTS

| | | | | |
|---|---|---|---|---|
| 3,633,413 A | * | 1/1972 | Case ........................ | 73/141 R |
| 3,893,330 A | * | 7/1975 | Shute et al. ..................... | 73/9 |
| 4,098,111 A | * | 7/1978 | Hardmark et al. ............... | 73/9 |
| 4,212,063 A | * | 7/1980 | Hardmark .................... | 364/426 |
| 4,315,426 A | * | 2/1982 | Brandon ......................... | 73/9 |
| 4,594,878 A | * | 6/1986 | Abe et al. ........................ | 73/9 |
| 4,662,211 A | * | 5/1987 | Strong .............................. | 73/9 |
| 4,958,512 A | * | 9/1990 | Johnsen ........................... | 73/9 |
| 5,561,244 A | * | 10/1996 | Olesky et al. ................. | 73/146 |
| 6,192,736 B1 | * | 2/2001 | Clem ............................... | 73/9 |
| 6,321,586 B1 | * | 11/2001 | Wojtowicz et al. .............. | 73/9 |

FOREIGN PATENT DOCUMENTS

JP        2001-183250     *  7/2001    ............. G01L/5/00

OTHER PUBLICATIONS

US 2001/0006002 A1 Patent Application Publication.*
Swedish National Road and Transport Research Institute, VTI Sartryck 290–1998.
Saab Friction Tester Engineering Specification (SAS), pp. 1–13.

* cited by examiner

Primary Examiner—Herzron Williams
Assistant Examiner—Charles D. Garber
(74) Attorney, Agent, or Firm—Armstrong, Westerman & Hattori, LLP

(57) ABSTRACT

Provided is a road surface friction coefficient measuring method and device for measuring the friction coefficient of road surfaces such as roads and runways, and which can be used by being mounted on a general car. This device has a spindle 5 detachably connected to the wheel of a travelling wheel 3 of a car, a support arm 6 oscillatably connected to the spindle, and a measuring wheel supported rotatably by the support arm. Provided to the support arm 6 are a vertical load generating mechanism for applying a vertical load to be added to the self weight of the measuring wheel 8, a first detection unit for detecting the vertical load that is applied to the measuring wheel from the road surface, a rotation transmission mechanism for transmitting to the measuring wheel the rotation of the spindle so as to provide a circumferential velocity difference between the travelling wheel and the measuring wheel, and a second detection unit for detecting the rotational resistance incurred by the measuring wheel from the road surface. The road surface friction coefficient is calculated with a computing unit based on the self weight of the measuring vehicle including the detected values of these detection units and the arm.

7 Claims, 3 Drawing Sheets

ROAD SURFACE FRICTION MEASURING METHOD AND DEVICE THEREFOR

BACKGROUND OF THE INVENTION

1. Field of the Invention

The present invention is directed to a road surface friction coefficient measuring method and device therefor to be utilized in managing the surface of roads on which vehicles such as a car travel or of airport runways.

2. Description of the Related Art

Conventionally, the measurement of the road surface friction coefficient for managing roads and airport runways was ordinarily conducted by running a measuring vehicle comprising a measuring device. For example, with the measuring vehicle 31 shown in FIG. 4 and FIG. 5, a front-wheel-drive vehicle is remodeled and a measuring wheel 33 for measuring the friction coefficient of the road surface G is provided inside the rear trunk room 32. This measuring wheel 33 comprises at the periphery thereof a tire having proximate characteristics of a tire of cars or aircraft that travel on the road surface G, and is mounted on the axle 35 of the travelling wheel 34 via a support arm 36.

The front end of the support arm 36 is rotatably connected to the axle 35 and the rear end thereof supporting the measuring wheel 33 is vertically oscillatable. The measuring wheel 33 contacts the road surface G pursuant to its own weight and the weight of the support arm 36 at the time of measurement. Moreover, rotation of the rear travelling wheel 34 is transmitted to the measuring wheel 33 via a rotation transmission mechanism not shown provided within the support arm 36. Here, when the travelling wheel 34 rotates on the road surface G without slipping due to the difference in the circumferential velocity of the measuring wheel and the circumferential velocity of the travelling wheel, the measuring wheel 33 is structured so as to rotate while slipping on the road surface G at a prescribed slip ratio.

When the measuring wheel 33 travels on the road surface G while slipping, the rotational resistance incurred by the measuring wheel 33 due to the friction with the road surface G is detected by a torque detection means provided within the aforementioned rotation transmission mechanism. A computing device 37 successively calculates the sliding friction of the road surface G to the measuring wheel 33 pursuant to the value detected by the torque detection means described above and the value of the vertical load of the measuring wheel 33 on the road surface incurred by the support arm 36 and its own weight. This calculation result is indicated on the display installed in the measuring vehicle or printed with a printer. Further, a measurement method wherewith a tractional car is equipped with the above-mentioned measurement device has also been conducted heretofore.

Moreover, as another conventional method of measuring the friction coefficient of the road surface, a method is known wherein a tractional measuring vehicle with a pair of wheels mutually facing opposite directions obliquely to the travelling direction is connected to the rear portion of a vehicle to be tracted along the road surface. In this tractional measuring car, the mutually inclined wheels are rotatably mounted respectively to a pair of frames connected in an approachable/separable manner. A load cell is disposed between these frames and this load cell detects the frictional force acting upon the horizontal direction of the respective wheels inclined from the road surface when the tractional measuring car travels on the road surface. The friction coefficient is thereby calculated based on this detected value and the value of the vertical load acting upon the respective wheels from the road surface due to the self weight of the tractional measuring car.

In addition, as another method for measuring the road surface friction coefficient, known is a method of running a vehicle equipped with an accelerometer on the road surface to be measured and measuring the friction coefficient from the deceleration (negative acceleration) upon applying brakes.

With the aforementioned method of measuring the friction coefficient of a road surface utilizing the measuring car shown in FIG. 4 and FIG. 5, the measuring car has a special structure in which a measuring wheel is provided inside the trunk room, and there is a problem in that the costs for remodeling the vehicle body becomes high. Further, upon measuring the friction coefficient of a road surface by tracting a tractional measuring vehicle with a car, it is necessary to make the measuring vehicle heavy to a certain degree such that the wheel can obtain the vertical load from the road surface. As a result, there is a problem in that the size of the measuring vehicle becomes large and the influence of the tractional car becomes great. Moreover, with the tractional car having a pair of wheels arranged obliquely to the travelling direction, there is a problem in that such type of tractional car is inappropriate for measuring snow/ice road surfaces because, in addition to the frictional force acting from the resisting force upon the. wheels oblique to the travelling direction of the measuring vehicle, the resisting force arising from proceeding while scraping the snow and ice is also applied.

Further, with the method of measuring the friction coefficient of a road surface with a car equipped with an accelerometer, there is a problem in that differences arise in the measured values due to the manner of applying the brakes. In addition, it is not possible to use this method for continuous measuring the friction coefficient of airport runways, and there is a problem in that this method can only be used in a limited context.

SUMMARY OF THE INVENTION

An object of the present invention i s to resolve the problems of the conventional technology described above, and to provide a road surface friction coefficient measuring method and device therefor which can be used by being easily installed in a general car and is capable of measuring the friction coefficient of various road surfaces, such as roads and runways, at a high degree of accuracy.

A road surface friction coefficient measuring method according to the present invention for achieving the aforementioned object comprises the steps of: providing a measuring wheel on the outside of the travelling wheel of a car via a support arm provided oscillatably about the axis line of the travelling wheel; generating frictional force of the ground surface to the measuring wheel by rotatably driving the measuring wheel so as to have a prescribed difference in circumferential velocity from the travelling wheel; applying a vertical load to be added to the self weight of the measuring wheel by applying a prescribed vertical load to the measuring wheel; and measuring the frictional force and the vertical load and calculating the road surface friction coefficient based on the measured values.

And a road surface. friction measuring device according to the present invention for achieving the aforementioned road surface friction coefficient measuring method comprises: a spindle connected and secured to the outside of a travelling wheel of a car on the axis line to the axle; a support arm in which one end thereof is rotatably connected about the axis line of the spindle and the other end thereof is supporting the axle of measuring wheel; a measuring wheel rotatably supported about the axis line parallel to the spindle at a position apart from the spindle at the other end of the support arm; a rotation transmission mechanism for transmitting to the measuring wheel the rotation of the spindle so as to provide a prescribed circumferential velocity difference between the travelling wheel and measuring wheel; a vertical load generating mechanism for applying a vertical load to be added to the self weight of the measuring wheel; first detection means for detecting the vertical load; second detection means for detecting the frictional force upon the measuring wheel slipping and rotating on the road surface; and computing means for calculating the slip friction coefficient to the road surface and measuring wheel based on the detected values respectively obtained from the first detection means and second detection means and the self weight of the measuring wheel including the arm.

By mounting the spindle detachably on the wheel of the travelling wheel, the device can be easily installed in a general car. Employed as the rotation transmission mechanism may be one among a gear train transmission mechanism, chain transmission mechanism, bevel gear transmission mechanism, or belt transmission mechanism. The vertical load generating mechanism may, for example, comprise a disk brake mechanism in which a brake disk is secured to the spindle side and a caliper is provided on the support arm side, apply braking force to the travelling wheel from the support arm, and generate a vertical load to be added to the self weight of the measuring wheel as a reactive force. In addition, adequately employed as a vertical load generating mechanism may be a structure in which a power generator is provided to the support arm side and which obtains braking force by power generation upon rotating the power generator with the spindle, or a structure having a counter weel.

DESCRIPTION OF THE PREFERRED EMBODIMENTS

Figure 1:
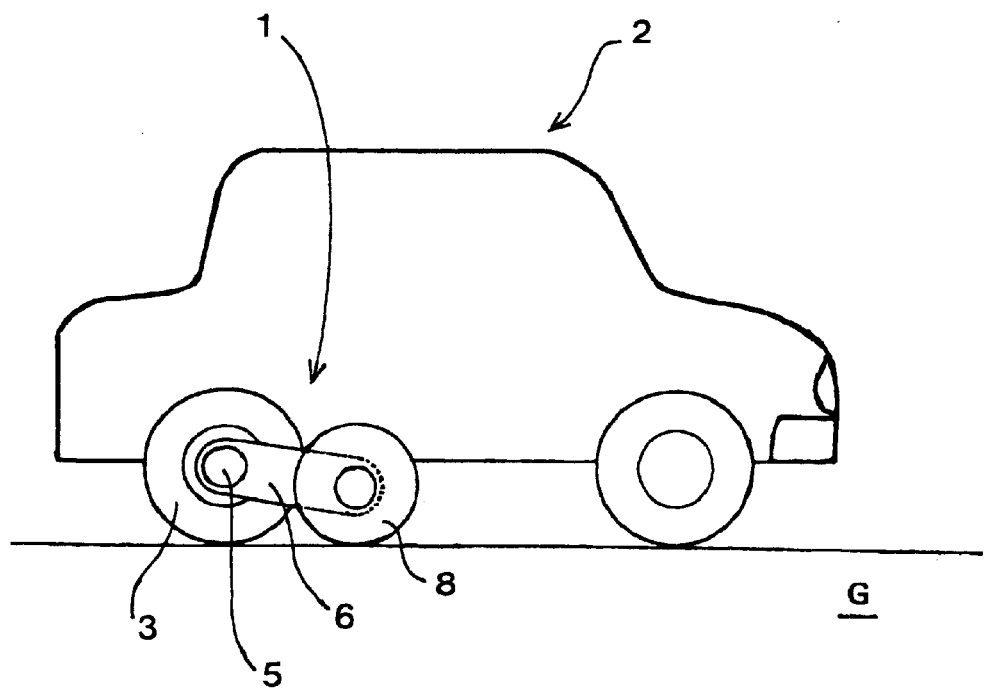
FIG. 1 is a side view showing the schematic structure of a car equipped with a road surface friction measuring device of the present invention.
Figure 2:
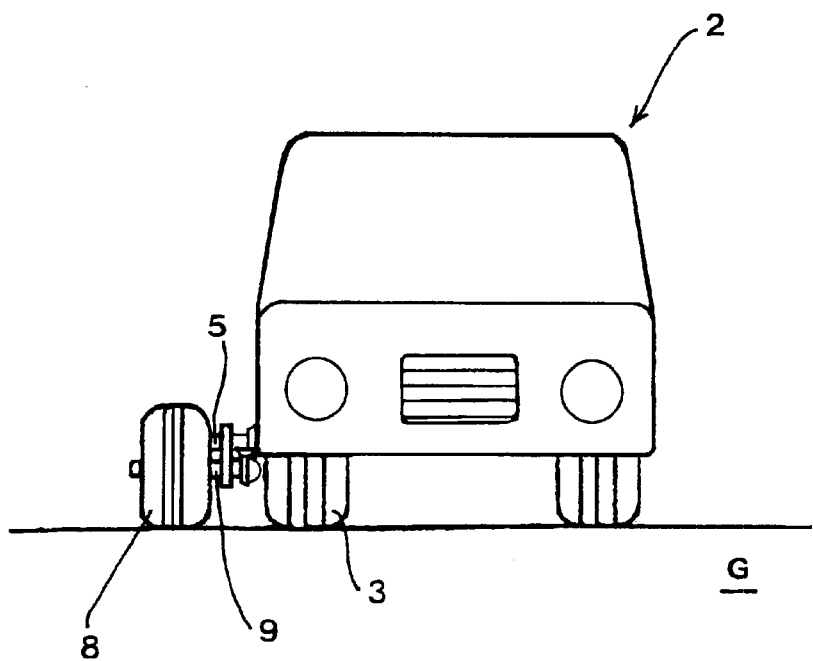
FIG. 2 is a front view showing the schematic structure of a car equipped with a road surface friction measuring device of the present invention.
Figure 3:
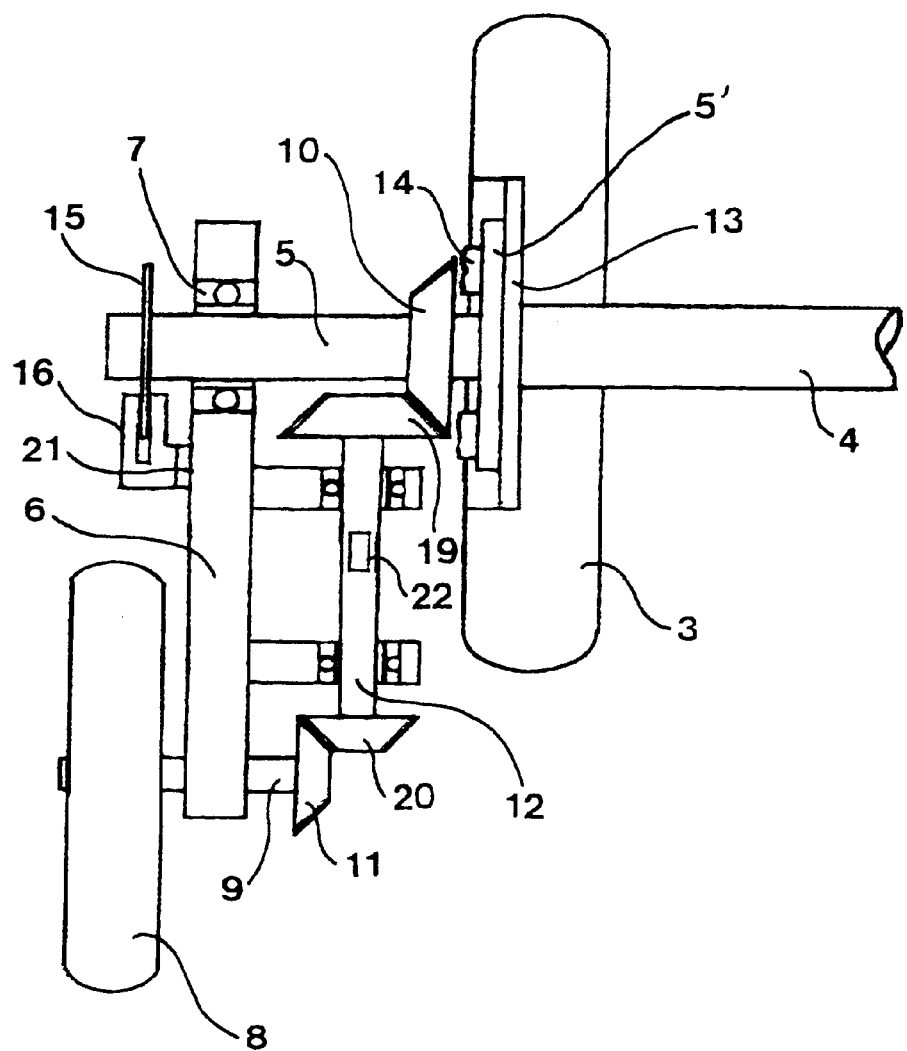
FIG. 3 is a plan schematic of the substantial parts thereof.
Figure 4:
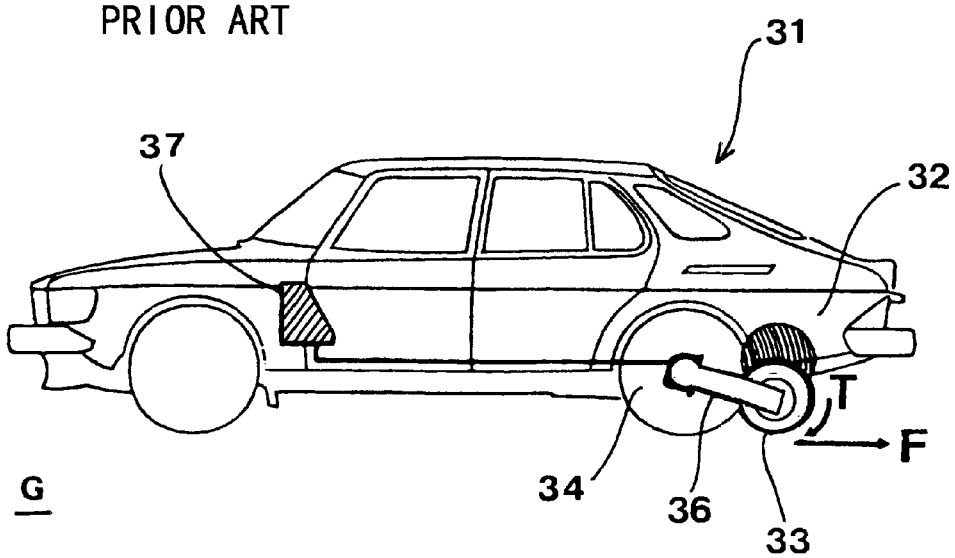
FIG. 4 is a side view showing the schematic structure of a car equipped with a conventional road surface friction measuring device.
Figure 5:
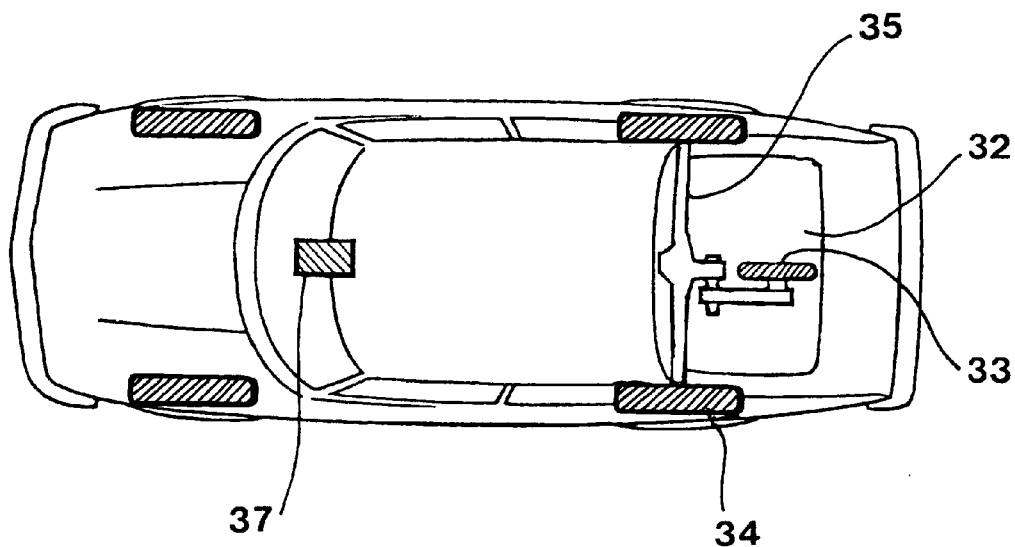
FIG. 5 is a plan view showing the schematic structure of a car equipped with a conventional road surface friction measuring device.

The embodiments of the present invention are now described in detail with. reference to the relevant drawings. FIG. 1 is a side view of a car equipped with the road surface friction measuring device of the present invention, and FIG. 2 is the front view thereof and FIG. 3 is a typical plan view of the substantial parts thereof. The road surface friction measuring device 1 is used by being detachably secured and connected to the wheel of a travelling wheel 3 on one side of the measuring vehicle 2. As the measuring vehicle 2 used for measuring the road surface friction coefficient, general vehicles such as passenger cars may be used.

The road surface friction measuring device 1 of this embodiment has a spindle 5 on the outside of the rear travelling wheel 3, which is the drive wheel, mounted on the axle 4 (FIG. 3) thereof. The spindle 5 is detachably secured to the travelling wheel 3 so as to protrude toward the outside of such travelling wheel 3 in a cantilever manner. In this embodiment, a mounting flange 5' is formed on one end of this spindle 5 and detachably secured to the wheel 13 of the travelling wheel with a plurality of bolts 14, and the spindle 5 rotates integrally with the axle 4. Nevertheless, the means for connecting the axle 4 and spindle 5 is not limited thereto. Moreover, one end of a support arm 6 is rotatably connected about the axis line of the spindle 5 via a ball bearing 7, and the other end of the support arm 6 is directed toward the front of the measuring vehicle so as to be capable of oscillating within the vertical plane about the spindle 5.

A measuring wheel axis 9, to which the measuring wheel 8 is secured in parallel to the axis line of the spindle 5, is rotatably supported by the other end of the support arm 6. Mounted on the periphery of the measuring wheel 8 is a tire with characteristics similar to the tire of the car traveling on the road surface G. Moreover, when the road surface G to be measured is a runway, mounted on the measuring wheel 8 may be a tire with characteristics of the tire of aircraft landing on and taking off from this road surface G.

The measuring wheel axis 9 to which the measuring wheel 8 is secured is structured to receive the transmission of the rotation of the spindle 5 via a rotation transmission mechanism built in the support arm 6.

In this embodiment, the rotation transmission mechanism is structured of an inboard bevel gear 10 secured to the spindle 5, an outboard bevel gear 11 secured to the measuring axis 9, and bevel gears 19 and 20 secured to the drive shaft 12 connected between the inboard and outboard bevel gears. With the rotation transmission mechanism, the measuring wheel 8 is made to rotate at a smaller circumferential velocity than that o f the travelling wheel 3 when the travelling wheel 3 rotates in connection with the running of the measuring vehicle 2.

Moreover, provided between the support arm 6 and the spindle 5 is a disk brake as the vertical load generating mechanism for applying a prescribed vertical load by the support arm 6 to the spindle 5. This disk brake has a brake disk 15 secured to the spindle 5 and a caliper 16 supported on the support arm side. Between the caliper 16 and the support arm 6, a load cell 21 as the first detection means of the present invention is provided for detecting the reactive force incurred upon the caliper 16 sandwiching the brake disk 15 from both sides and braking.

When the measuring vehicle 2 is running on the road surface G, the brake disk applies rotational resistance by braking the spindle and makes the momentum that presses the measuring wheel 8 against the road surface G to the support arm 6 as a counteraction. Therefore, the measuring wheel 8 is pressed against the road surface G by the momentum and the self weight of the support arm 6 and measuring wheel 8, and the counteraction thereof acts as the vertical load of the measuring wheel 8.

Meanwhile, the measuring wheel 8 slips on the road surface G at a prescribed slip ratio due to the difference in the circumferential velocity of the travelling wheel 3 and the measuring wheel 8. Thereupon, rotational resistance is added to the measuring wheel 8 due to the frictional force incurred by the measuring wheel 8 from the road surface G in accordance with the vertical load. In this embodiment, the rotational resistance is detected as the torque imparted to the drive shaft. Specifically, the rotational resistance is detected with a load cell or strain gauge 22 as the second detection means of this invention mounted on the shaft.

The detection outputs of the first detection means and the second detection means are sent to the microprocessor inside the measuring vehicle 2 via a signal cable not shown. Thereafter, calculation processing is conducted to such detection outputs in order to obtain the slip friction coefficient of the road surface G to the measuring wheel 8. The calculation results may be indicated on a display installed in the measuring vehicle 2 or printed by connecting the microprocessor to a printer.

Furthermore, although the microprocessor constitutes the computing means in this embodiment, the microprocessor may be installed in a car or built in the support arm. Moreover, a personal computer such as a laptop computer may be connected to the computing means in order to input the signals output from the first detection means and the second detection means via an interface compatible therewith. In the event of installing the computing means in the vehicle, the transmission of signals between the first detection means/second detection means and the computing means can be conducted via wire or wireless by utilizing a signal cable, telemeter, and so on.

The road surface friction measuring device of this embodiment is structured as described above and can measure the friction coefficient of a road surface by being connected to a vehicle body and running on a road or runway without having to specially remodel a general vehicle such as a passenger car. The measurement of the road surface friction coefficient is conducted by mounting the road surface friction measuring device on the outside of the travelling wheel of a car and running such car.

By the travelling wheel 3 of the car rotating without slipping on the road surface, the spindle 5 integrally rotates therewith and such rotation is transmitted to the measuring wheel 8 via the rotation transmission mechanism. The measuring wheel 8 rotates at a rotational speed so as to generate a predetermined difference in the circumferential velocity from the travelling wheel 3 of the car. Therefore, a prescribed slip ratio is applied pursuant to the difference in the circumferential velocity of the travelling wheel of the car and the measuring wheel, frictional force acts upon the moving measuring wheel 8 from the road surface, and this becomes the rotational resistance of the measuring wheel 8. The force which applies the slip ratio is equivalent to the ground surface frictional force.

The force which applies the slip ratio is detected by the second detection means. A strain gauge 22 attached to the drive shaft is used as the second detection means in this embodiment and, by detecting the rotational torque acting upon the transmission rod pursuant to the strain gauge, the rotational resistance of the measuring wheel is measured and the ground surface frictional force acting upon the measuring wheel from the road surface is indirectly measured.

Further, while measuring the road surface friction coefficient, brake is applied to the spindle 5 by the vertical load generation mechanism (disk brake in this embodiment) for applying a vertical load from the support arm 6 side to the spindle. Pursuant to this counteraction, momentum that presses the measuring wheel 8 to the road surface G acts upon the support arm 6 provided facing the forward travelling direction. Nevertheless, the braking force of the spindle resulting from the vertical load generating mechanism for applying a vertical load must be within a range which will not cause a large slip to the travelling wheel 3. In addition to the load from the momentum, load from the self weight of the support arm 6 and measuring wheel 8 also acts upon the road surface, and the counteraction of these loads is applied as the vertical load necessary in measuring the road surface friction coefficient. By detecting the reactive force incurred by the caliper 16 provided to the support arm 6 with the first detection means, the vertical load added to the measuring wheel 8 is indirectly measured.

The detected value of the aforementioned first detection means relates to the size of the vertical load incurred by the measuring wheel from the road surface, and the detected value of the second detection means relates to the frictional force acting upon the measuring wheel from the road surface. Thus, by inputting to the computing means these detected values as well as the self weight of the measuring wheel, the computing means calculates the added vertical load incurred by the measuring wheel from the road surface upon correcting the weight of the support arm and measuring wheel in view of the detected value of the first detection means, calculates the frictional force acting upon the measuring wheel from the road surface corresponding to the detected value of the second detection means, and calculates the slip friction coefficient of the road surface to the measuring wheel.

Although a preferred embodiment of the present invention was described above, this invention is not limited to the aforementioned embodiment and may be changed within the range of the technical idea thereof.

For instance, without restriction to the bevel gear rod mechanism of the aforementioned embodiment as the rotation transmission mechanism, employed may be a chain transmission mechanism, gear train transmission mechanism, or belt transmission mechanism such as a timing belt. Moreover, as the vertical load generating mechanism, without restriction to the mechanism which generates a vertical load by applying braking force to the travelling wheel side from the support arm side and using the counteraction thereof, employed may be a suitable mechanism for generating to the support arm the rotational momentum in the direction of pressing the measuring wheel to the road surface, or a mechanism which adds a direct vertical load with a plumb bob. Further, in addition to the brake disk mechanism for generating a vertical load by applying braking force to the travelling wheel side from the support arm side and using the counteraction thereof, employed may be, for example, an electronic brake having a structure in which a power generator is provided to the support arm side, and which obtains braking power by power generation by rotating the spindle thereby, and so forth.

As described above, according to the road surface friction coefficient measuring method and device therefor of the present invention, there is no need to use a costly special vehicle that is remodeled for measuring the road surface friction coefficient. As the present invention may be used by connecting it to a travelling wheel of ordinary vehicles such as passenger cars, it is possible to measure the road surface friction coefficient easily, and with low cost.

As it is possible to add a prescribed vertical load to be added to the self weight of the measuring wheel, the bouncing of the measuring wheel can be reduced and changes in the vertical load of the measuring wheel can be detected thereby. As a result, the road surface friction measuring device can be downsized as the weight thereof can be reduced, and the precision is improved.

Moreover, as the road surface friction is calculated based on the vertical load and rotational resistance acting from the road surface on the measuring wheel that is constantly facing the travelling direction, the measurement is not influenced by the characteristics of the travelling wheel or the braking operation of the vehicle itself conducting the measurement as when measuring the road surface friction coefficient from the deceleration of a car utilizing an accelerometer. Further, it is possible to obtain highly accurate measurement results even on snow/ice roads.

What is claimed is:

1. A road surface friction coefficient measuring method, comprising the steps of:

providing a measuring wheel on the lateral outside of the traveling wheel of a car via a support arm provided oscillatably about the axis line of said traveling wheel;

generating frictional force of said measuring wheel to the ground surface by rotatably driving said measuring wheel so as to have a prescribed difference in circumferential velocity with said traveling wheel;

generating a vertical load to be added to the self weight of said measuring wheel by applying a prescribed vertical load to said measuring wheel; and measuring said frictional force and said vertical load and calculating the road surface friction coefficient based on said measured values.

2. A road surface friction measuring device, comprising a spindle connected and secured to the outside of a traveling wheel of a car on the axis line to the axle;

a support arm one end of which is rotatably connected about the axis line of said spindle and the other end of which is provided to be vertically oscillatable;

a measuring wheel rotatably supported about the axis line parallel to the spindle at a position apart from the spindle at said other end of said support arm;

a rotation transmission mechanism for transmitting to the measuring wheel the rotation of the spindle so as to provide a prescribed difference in circumferential velocity between said traveling wheel and measuring wheel;

a vertical load generating mechanism for applying a vertical load to be applied to the self weight of said measuring wheel;

first detection means for detecting said vertical load;

second detection means for detecting the frictional force upon said measuring wheel slipping and rotating on the road surface; and computing means for calculating the slip friction coefficient to the road surface and measuring wheel based on the detected values respectively obtained from the first detection means and second detection means and the self weight of the measuring wheel including the arm.

3. A road surface friction measuring device according to claim 2, wherein said spindle is detachably mounted on the wheel of the traveling wheel.

4. A road surface friction measuring device according to claim 2 or claim 3, wherein said rotation transmission mechanism comprises one among a gear train transmission mechanism, chain transmission mechanism, bevel gear transmission mechanism, or belt transmission mechanism.

5. A road surface friction measuring device according to claim 2 or claim 3, wherein said vertical load generating mechanism comprises a disk brake mechanism in which a brake disk is secured to said spindle side and a caliper is provided on the support arm side, so that braking force is applied to said traveling wheel from said support arm, a vertical load to be added to the self weight of the measuring wheel is generated as a reactive force.

6. A road surface friction measuring device according to claim 2 or claim 3, wherein said vertical load generating mechanism is of a structure in which a power generator is provided to said support arm side and braking force is obtained from power generated by rotating said power generator with said spindle.

7. The road surface friction coefficient measuring method according to claim 1, comprising mounting the measuring wheel on the outside of the traveling wheel.

* * * * *